United States Patent [19]
Whitfield et al.

[11] Patent Number: 5,470,338
[45] Date of Patent: Nov. 28, 1995

[54] INSTRUMENT FOR CLOSING TROCAR PUNCTURE WOUNDS

[75] Inventors: Kenneth H. Whitfield, New Haven; Ian M. Scott, Ridgefield; Michael Castro, Seymour, all of Conn.

[73] Assignee: United States Surgical Corporation, Norwalk, Conn.

[21] Appl. No.: 134,144

[22] Filed: Oct. 8, 1993

[51] Int. Cl.⁶ .................................................. A61B 17/00
[52] U.S. Cl. ........................... 606/144; 606/139; 606/148; 112/169
[58] Field of Search .................................. 606/139, 144, 606/145, 146, 147, 148, 151, 208; 112/169, 80.03

[56] References Cited

U.S. PATENT DOCUMENTS

| | | |
|---|---|---|
| 385,586 | 7/1888 | Woods ................................. 606/146 |
| 1,037,864 | 9/1912 | Carlson et al. . |
| 1,449,087 | 3/1923 | Bugbee . |
| 1,822,330 | 9/1931 | Ainslie . |
| 2,108,206 | 2/1938 | Meeker . |
| 2,213,830 | 9/1940 | Anastasi . |
| 2,579,192 | 12/1951 | Kohl . |
| 2,601,564 | 6/1952 | Smith . |
| 2,737,954 | 3/1956 | Knapp . |
| 2,959,172 | 11/1960 | Held . |
| 3,090,386 | 5/1963 | Curtis . |
| 3,168,097 | 2/1965 | Dormia . |
| 3,470,875 | 10/1969 | Johnson . |
| 3,807,407 | 4/1974 | Schweizer . |
| 3,871,379 | 3/1975 | Clarke . |
| 3,901,244 | 8/1975 | Schweizer . |
| 4,345,601 | 8/1982 | Fukuda . |
| 4,493,323 | 1/1985 | Albright et al. . |
| 4,510,934 | 4/1985 | Batra . |
| 4,557,265 | 12/1985 | Andersson . |
| 4,597,390 | 7/1986 | Mulhollan et al. . |
| 4,621,640 | 11/1986 | Mulhollan et al. . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 4,986,825 | 1/1991 | Bays et al. . |
| 5,129,912 | 7/1992 | Noda et al. . |
| 5,152,769 | 10/1992 | Baber . |
| 5,211,650 | 5/1993 | Noda ..................................... 606/148 |
| 5,222,508 | 6/1993 | Contarini . |
| 5,306,280 | 4/1994 | Bregen et al. ......................... 606/143 |
| 5,314,424 | 5/1994 | Nichols ................................. 606/208 |
| 5,320,632 | 6/1994 | Heidmueller . |
| 5,364,408 | 11/1994 | Gordon . |
| 5,368,601 | 11/1994 | Sauer et al. . |

FOREIGN PATENT DOCUMENTS

| | | |
|---|---|---|
| 0140557 | 9/1984 | European Pat. Off. . |
| 0478949 | 4/1992 | European Pat. Off. . |
| 4137218 | 2/1993 | Germany . |
| 1093329 | 5/1984 | U.S.S.R. . |

*Primary Examiner*—Stephen C. Bellegrino
*Assistant Examiner*—Jeffrey A. Schmidt

[57] ABSTRACT

A novel surgical instrument for applying sutures through body tissue including an elongated body having a proximal end portion and a distal end portion, at least one needle carrier member operatively mounted in the distal end portion and movable between at least a retracted position and a deployed position, a needle releasably retained in the at least one needle carrier member, a predetermined length of suture material having one end affixed to the needle, and a suture material tensioning member disposed within the elongated body for maintaining the suture material in tension during movement of the at least one needle carrier member from the retracted position to the deployed position the suture material. The instrument may also include a retaining mechanism adapted to retain the at least one needle carrier in the partially deployed position, and a needle skewing mechanism operatively associated with an actuator member to change the alignment thereof relative to the retaining member. A deployment indicator may be provided to indicate to an operator of the instrument When the at least one needle carrier member is in the second position.

28 Claims, 10 Drawing Sheets

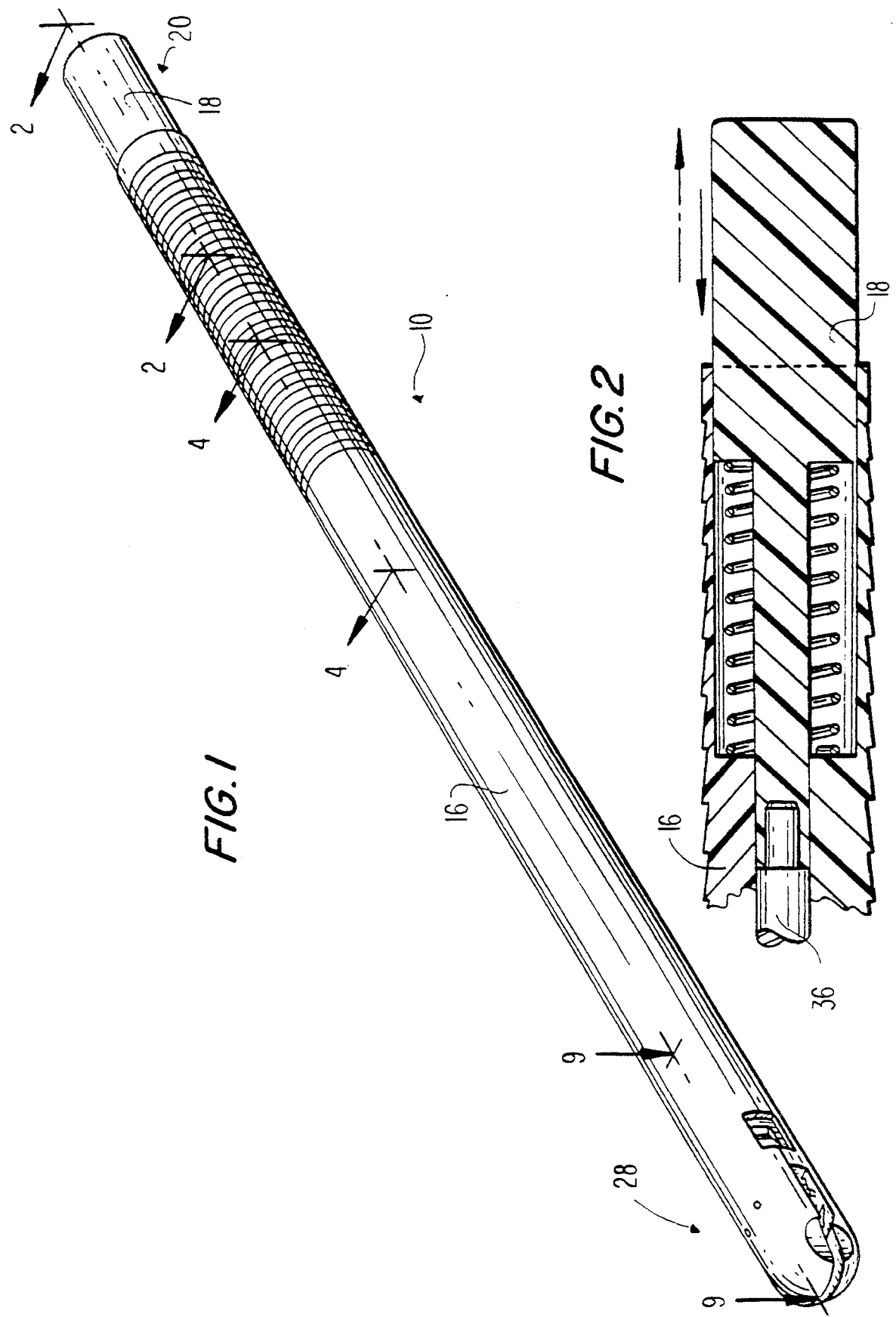

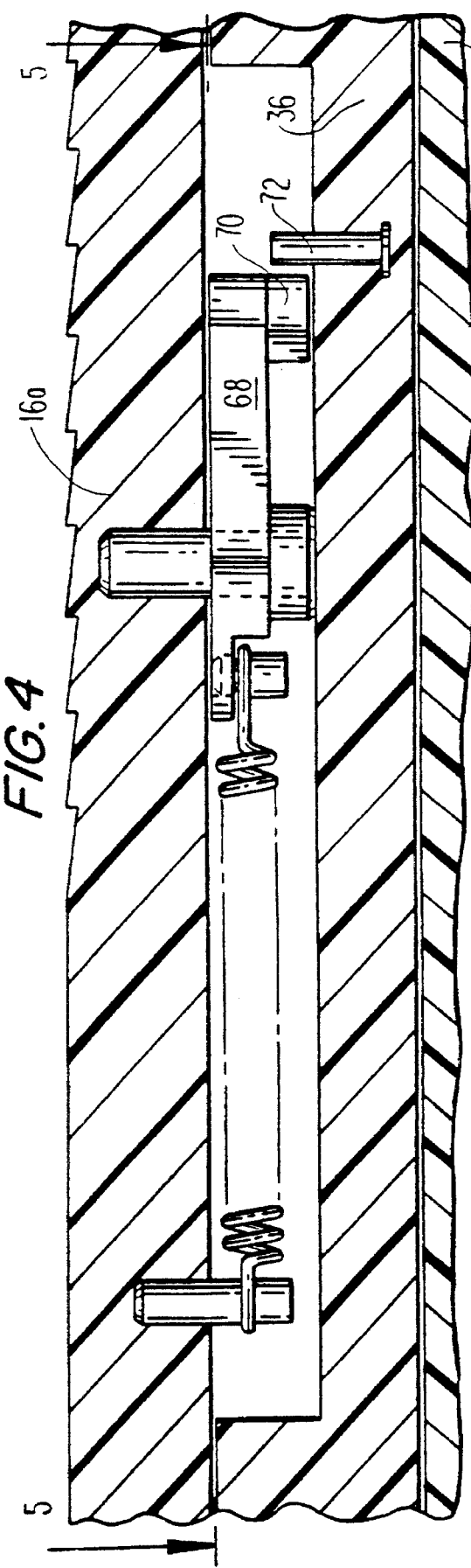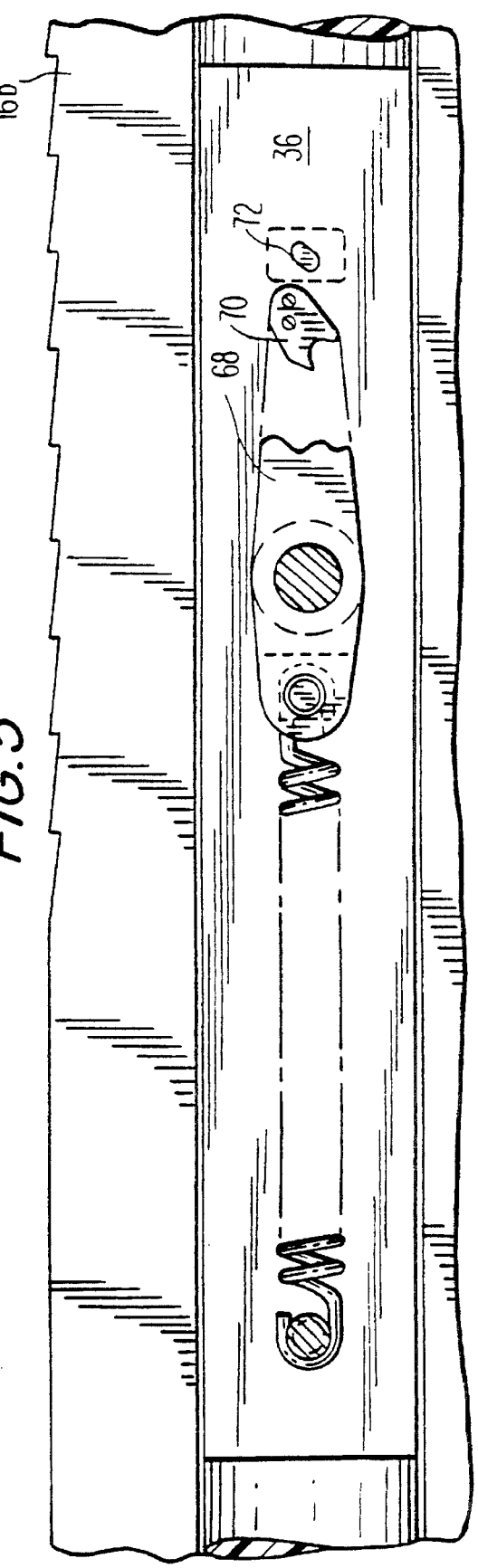

INSTRUMENT FOR CLOSING TROCAR PUNCTURE WOUNDS

BACKGROUND OF THE INVENTION

1. Field of the Invention

This invention relates to instruments for suturing puncture wounds and more particularly to instruments for closing trocar puncture wounds formed during endoscopic surgical procedures.

2. Description of the Related Art

With laparoscopic and endoscopic surgery, a small incision or puncture is made in the patient's body to provide access for a tube or a cannula device. Once extended into the patient's body, the cannula allows for insertion of various surgical instruments such as scissors, dissectors, retractors, or biopsy instruments to perform diagnostics and/or surgery. Upon completion of the surgical procedure, the remaining trocar wound may require some attention, e.g., in the form of placing sutures to close the wound. In certain cases it may be desirable to close the wound from within.

A device which forms sutures from within the urethra is shown in Soviet Patent SU 1093329. The device is inserted into the urethra and pivotally deploys needles from which sutures are subsequently pulled through the side walls of the urethra.

Other devices have been developed which are used to place sutures from within a wound. For example, commonly assigned applications Ser. No. 07/950,073 filed Sep. 23, 1992, now abandoned and Ser. No. 08/013,244 filed Feb. 23, 1993, now U.S. Pat. No. 5,403,328 as well as application Ser. No. 07/876,511, now U.S. Pat. No. 5,368,601 relate to different surgical instruments for placing sutures from within a trocar wound. U.S. patent application Ser. No. 08/091,793, filed Jul. 14, 1993 also discloses a surgical instrument for placing suture, the contents of which are incorporated herein by reference. Also, a device has been developed for placing sutures from within a trocar wound which includes a needle clamping device for capturing the needles upon deployment thereof. Such a device is shown in a product brochure of REMA-Medizintechnik GmbH of Germany.

Accordingly, a need exists, for an improved instrument which provides better deployment and capturing or shielding of the needles.

SUMMARY OF THE INVENTION

The present invention provides a novel surgical instrument for applying sutures through body tissue and includes a lightweight and easy to use instrument which may be operated quickly and efficiently.

In one aspect of the present invention, the instrument includes an elongated body having a proximal end portion and a distal end portion, at least one needle carrier member operatively mounted in the distal end portion and movable between at least a retracted position and a deployed position, a needle releasably retained in the at least one needle carrier member, a predetermined length of suture material having one end affixed to the needle. The instrument may include a suture material tensioning member disposed within the elongated body for maintaining the suture material in tension during movement of the at least one needle carrier member from the retracted position to the deployed position.

The instrument may also include a retaining mechanism adapted to retain the at least one needle carrier in the partially deployed position.

In another aspect of the present invention, the instrument includes an actuator member operatively associated with the at least one needle carrier member, the actuator member being movable between at least a first position and a second position to move the at least one needle carrier from the initial position to the deployed position, a needle retaining member disposed in the elongated body and adapted to retain the needle therein when the at least one needle carrier member is in the deployed position, and a needle skewing mechanism operatively associated with the actuator member such that upon movement of the actuator member from the first position to the second position the needle skewing mechanism contacts a tapered portion of the needle to change the alignment thereof relative to the retaining member.

A deployment indicator may be included in the instrument to provide an indication to an operator of the instrument when the at least one needle carrier member is in the second position.

BRIEF DESCRIPTION OF THE DRAWINGS

Preferred embodiments of the invention are described hereinbelow with reference to the drawings wherein:

FIG. 1 is a perspective view of one embodiment of the instrument of the present invention;

FIG. 2 is a partial cross-sectional view taken along section line 2—2 of FIG. 1;

FIG. 4 is a cross-sectional view taken along section line 4—4 of FIG. 1;

FIG. 5 is a cross-sectional view taken along line 5—5 of FIG. 4;

DETAILED DESCRIPTION OF THE PREFERRED EMBODIMENTS

Figure 3:
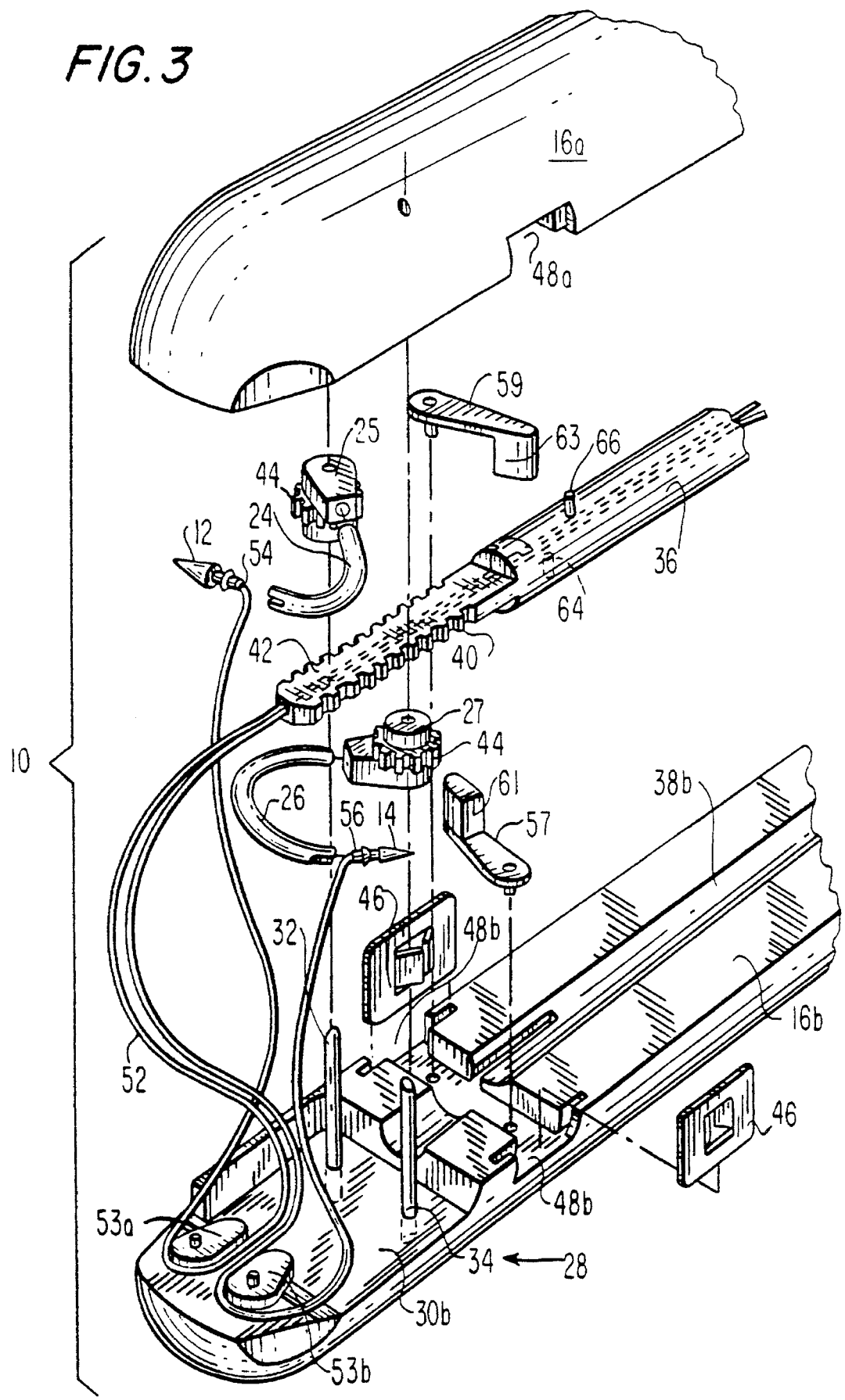
FIG. 3 is an exploded partial-view with parts separated of the distal end of the instrument of FIG. 1.

Referring now in specific detail to the drawings, in which like reference numerals identify similar or identical elements throughout the several views, and initially to FIGS. 1–3, one embodiment of a suturing instrument for closing puncture wounds in accordance with the present invention is shown generally at 10. Suturing instrument 10 is particularly adapted for driving a pair of needles 12 and 14 from within the endoscopic cavity of a patient into the peripheral tissue adjacent an endoscopic puncture wound and placing a suture therein. However, instruments which utilize more or less than two needles are also within the scope of the present invention.

Generally, suturing instrument 10 includes an elongated housing portion, for example, elongated tubular body 16 having actuator button 18 slidably disposed at proximal end 20 and needle deploying means such as needle carrier arms 24 and 26 mounted adjacent distal end 28. Elongated tubular body 16 is suitable for insertion preferably through a trocar cannula or alternately directly into a puncture wound such as a trocar incision wound formed during an endoscopic or laparoscopic surgical procedure. Except where noted otherwise, the materials utilized in the components of the instrument generally include such materials as polycarbonate for housing sections and related components, and stainless steel, particularly for components which transmit forces. One preferred material is a polycarbonate material available from General Electric Company under the trade name LEXAN. Other specific preferred materials such as nylon or glass filled nylon (for strength) may also be utilized. However, equivalent alternative materials will readily come to the mind of those skilled in the art.

In FIG. 3, distal end 28 of instrument 10 is shown with the component parts separated for illustration purposes. Elongated housing portion 16 includes housing half-sections 16a and 16b which are attached by any suitable means, such as for example, fasteners, adhesives, welding, etc. A pair of needles such as needles 12 and 14 are removably mounted such as by slip fitting them to carrier arms 24 and 26, respectively. Carrier arms 24 and 26 are mounted on gear members 25 and 27, respectively, which are operatively mounted on elongated housing portion 16 in cut out portions 30a and 30b formed in housing half sections 16a and 16b, respectively. Gear members 25 and 27 are preferably pivotally mounted on posts 32 and 34 respectively. A boss (not shown) is mounted on post 32 below gear member 25 and another boss (not shown) is mounted on post 34 above gear member 27. These bosses maintain gear members 25, 27 in the same plane.

An actuating member is provided, in the form of elongated rod 36 which is slidably positioned in a bore formed through elongated housing portion 16 and made up of grooves 38a (not shown) and 38b formed in housing half-sections 16a and 16b, respectively. Preferably, grooves 38a and 38b conform in shape to the outer surface of elongated rod 36 so as to facilitate sliding motion of elongated rod 36 within elongated housing portion 16. Elongated rod 36 is provided with teeth 40 formed on both side edges of flattened distal end portion 42. In the illustrated embodiment, distal end portion 42 is shown as being flattened, having a rectangular cross-section. Clearly, any suitable cross-section may be substituted for flattened distal end portion 42 or for rod 36.

Figure 12:
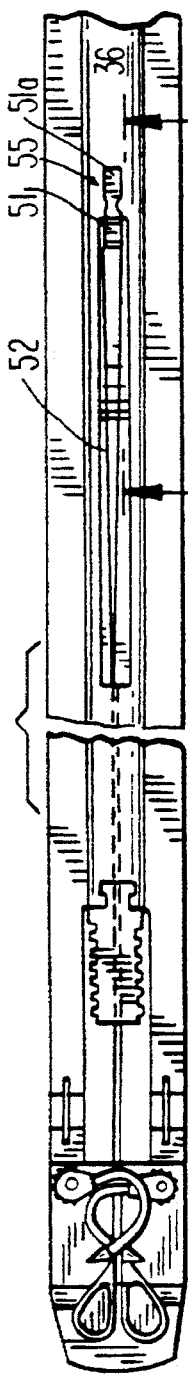
FIG. 12 is a partial plan view of the instrument of the present invention with one half of the elongated body removed to illustrate the suture material tensioning system.
Figure 13:
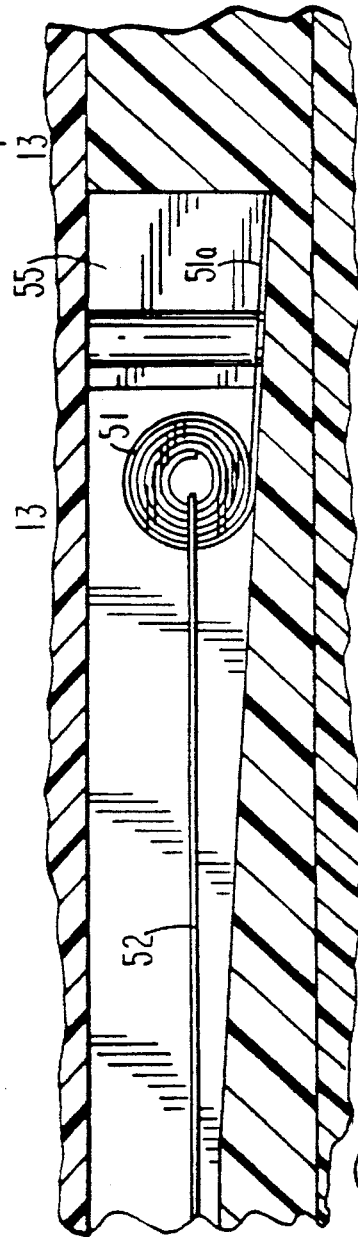
FIG. 13 is a cross-sectional view taken along section line 13—13 of FIG. 12.

Teeth 40 of elongated rod 36 cooperate, i.e. mesh, with teeth 44 of gear members 25 and 27 in a rack and pinion fashion so as to cause carrier arms 24 and 26 to pivot about posts 32 and 34, respectively. Needle retaining means are also provided in the form of latch members 46 which are inserted in slots formed in the walls of housing half sections 16a and 16b on either side of cutout portions 48a and 48b formed in housing half-sections 16a and 16b, respectively. Referring to FIGS. 12 and 13, a suture passageway is provided in elongated rod 36, shown as bore 50 formed along the central longitudinal axis of elongated rod 36 and passing partially therethrough. A suture tensioning member, shown as rolled constant force spring element 51, has tab portion 51a press fit into a cut-out portion 55 of elongated rod 36 so that tab 51a will remain fixed relative to elongated rod 36 upon actuation of instrument 10. Referring once again to FIG. 3, a suitable suture material such as suture 52 is thereby stored and fed through bore 50 (FIG. 15) and passes around suture guides 53a and 53b (FIG. 3) mounted between housing half-sections 16a and 16b, respectively, and spaced from the end of instrument 10 so that suture material 52 is not exposed at the bottom of the instrument. Suture 52 is attached to proximal ends 54 and 56 of needles 12 and 14, respectively.

Also mounted on elongated body 16 are needle kinking members such as arms 57 and 59 which are preferably pivotably mounted to housing half-section 16b. Clearly arms 57 and 59 could also be mounted one on each housing half section 16a and 16b or both on housing half-section 16a. Arms 57 and 59 have needle contacting surfaces extending therefrom such as extended portions 61 and 63, respectively. Camming pins 64 and 66 are preferably press fit into bores formed on opposite sides of elongated rod 36, as shown in FIG. 3. The operation of arms 57 and 59 in cooperation with camming pins 64 and 66 will be explained in detail further hereinbelow.

Figure 9:
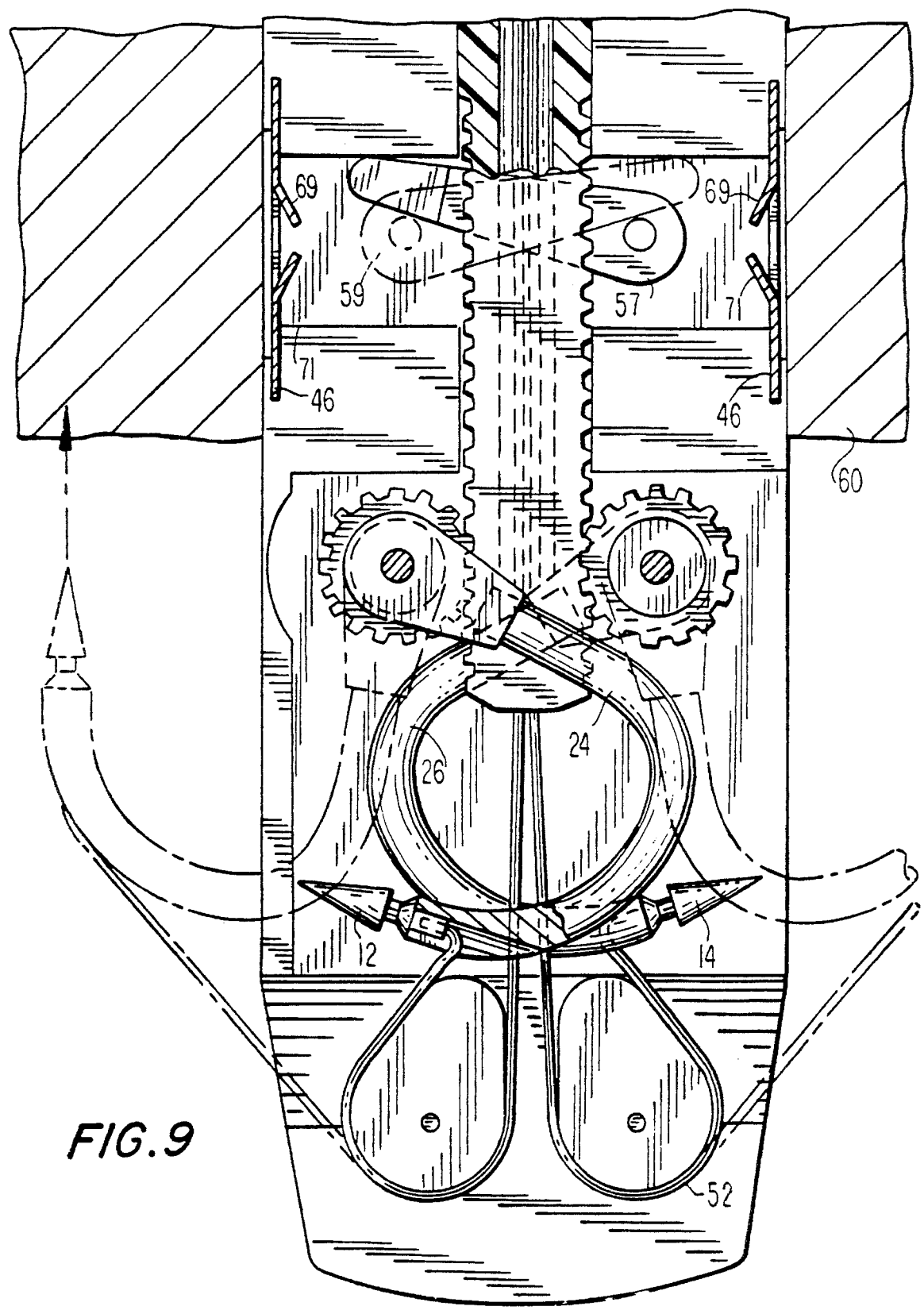
FIG. 9 is a cross-sectional view of the distal end of the instrument taken along section line 9—9 of FIG. 1 and showing the needle carriers in the intermediate position in phantom lines.

As shown in FIG. 2, elongated rod 36 is spring biased in a proximal direction corresponding to a retracted position of needles 12 and 14, illustrated in FIGS. 1 and 9. In the retracted position, needles 12 and 14 are preferably disposed completely within elongated housing portion 16. This facilitates insertion and removal of suturing instrument 10 without undesired contact of needle 12 and 14 with either the patient's tissue or that of the operating room personnel.

Referring now to FIGS. 4–8, the mechanism for retaining needle carriers 24 and 26 in the partially deployed position as shown in phantom lines in FIG. 9 will now be described. FIGS. 4 and 5 illustrate the various structural components of the retaining mechanism. Pivot arm 68 is pivotably mounted on housing half-section 16a and is spring biased to align parallel with a longitudinal axis of housing half-section 16a. Latch member 70 is securely mounted to the proximal end of pivot arm 68 or alternatively can be integral therewith. Post member 72 is mounted on elongated rod 36, preferably in line with the central longitudinal axis of pivot arm 68, so that post member 72 is situated immediately proximal to the proximal end of pivot arm 68 when the instrument is in the fully retracted position.

In operation, suturing instrument 10 is inserted, in its initial or fully retracted position, as shown in FIG. 9, in a puncture wound such as the type created by a trocar during endoscopic or laparoscopic surgical procedures. Preferably the instrument is inserted into the incision wound (in the direction of arrow A in FIG. 9) so that proximal end 58 of the opening formed by cutouts 30a and 30b is situated immediately below the fascia, designated as 60 in FIG. 9. Separate indicating means (not shown) may be provided on suturing instrument 10 to apprise the user as to when suturing instrument 10 is in the preferred position.

Alternatively, suturing instrument 10 may be inserted through an appropriately sized trocar situated in a body wall. Once suturing instrument 10 is adequately inserted, the trocar may be removed leaving suturing instrument 10 in place.

Figure 6:
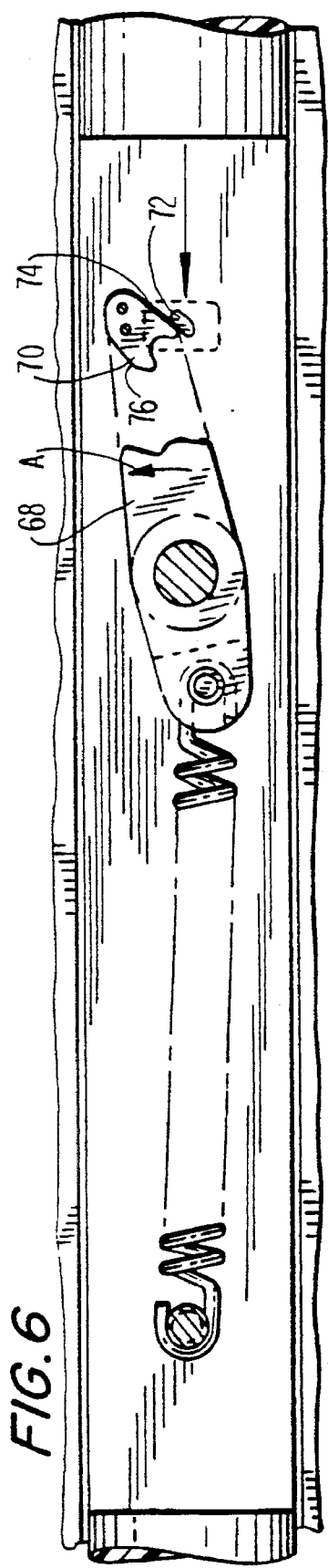
FIGS. 6–8 are views similar to FIG. 5, which show the sequential operation of the needle deployment actuating mechanism of the instrument of FIG. 1.
Figure 7:
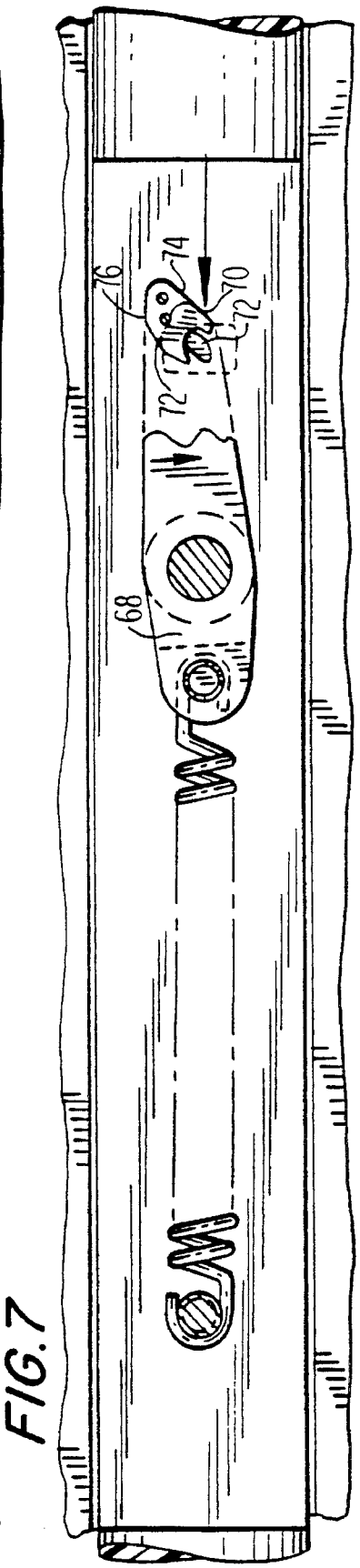

With suturing instrument 10 situated in the appropriate position, actuating button 18 (FIG. 1) is depressed thereby urging elongated rod 36 in a distal direction causing teeth 40 to rotate carrier arms 24 and 26, due to the meshing of teeth 40 with teeth 44 of the gear members 25 and 27. As actuator button 18 is depressed, post member 72, which as noted above is mounted to elongated rod 36, moves distally, as shown in FIG. 6. Post member 72 contacts leading edge 74 of latch member 70 and the camming action resulting from the sliding contact between the continued distal motion of post member 72 and leading edge 74 causes pivot arm to rotate counter-clockwise in the direction of Arrow A of FIG. 6. With continued distal motion of elongated rod 36, post member 72 passes becomes latched, as shown in FIG. 7. This position corresponds with the intermediate position of needle carrier arms 24 and 26 as shown in phantom lines in FIG. 9.

The initial rotation of needle carrier arms to their intermediate position causes suture material 52 to pull in a distal direction consequently causing rolled spring element 51 (FIGS. 12 and 13) to unravel slightly while maintaining tension in suture material 52.

Figure 8:
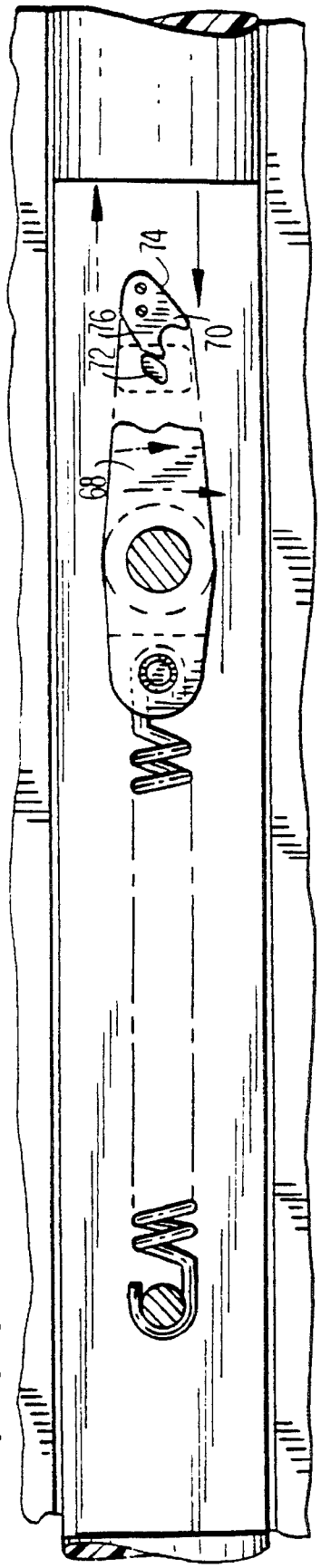

With the carrier arms disposed in the intermediate position, the user can then pull the instrument proximally toward the surface of the trocar incision and embed the needles in the fascia. Once the needles have been embedded in fascia 60, the instrument is then preferably fully deployed by depressing actuator button 18 to its distal-most position. Needles 12 and 14 are thereby rotated on carrier arms 24 and 26 such that needles 12 and 14 continue through fascia 60 allowing the needles to pass through a portion of the fascia and surrounding tissue. (See arrow B in FIG. 10). The complete depression of actuator button 18 causes post member 72 to move distally to disengage with latch member 74 enough so that the spring biased pivot arm 68 returns to its centrally aligned orientation, which causes latch member 74 to drop below post member 72, as shown in FIG. 8. Thus, when the appropriate time occurs, the release of actuator button and the resulting proximal movement of the spring biased elongated rod 36 will cause post member 72 to cam trailing edge 76 of latch member 70 such that post member 70 passes around latch member 70 and returns to its proximal-most position.

Figure 10:
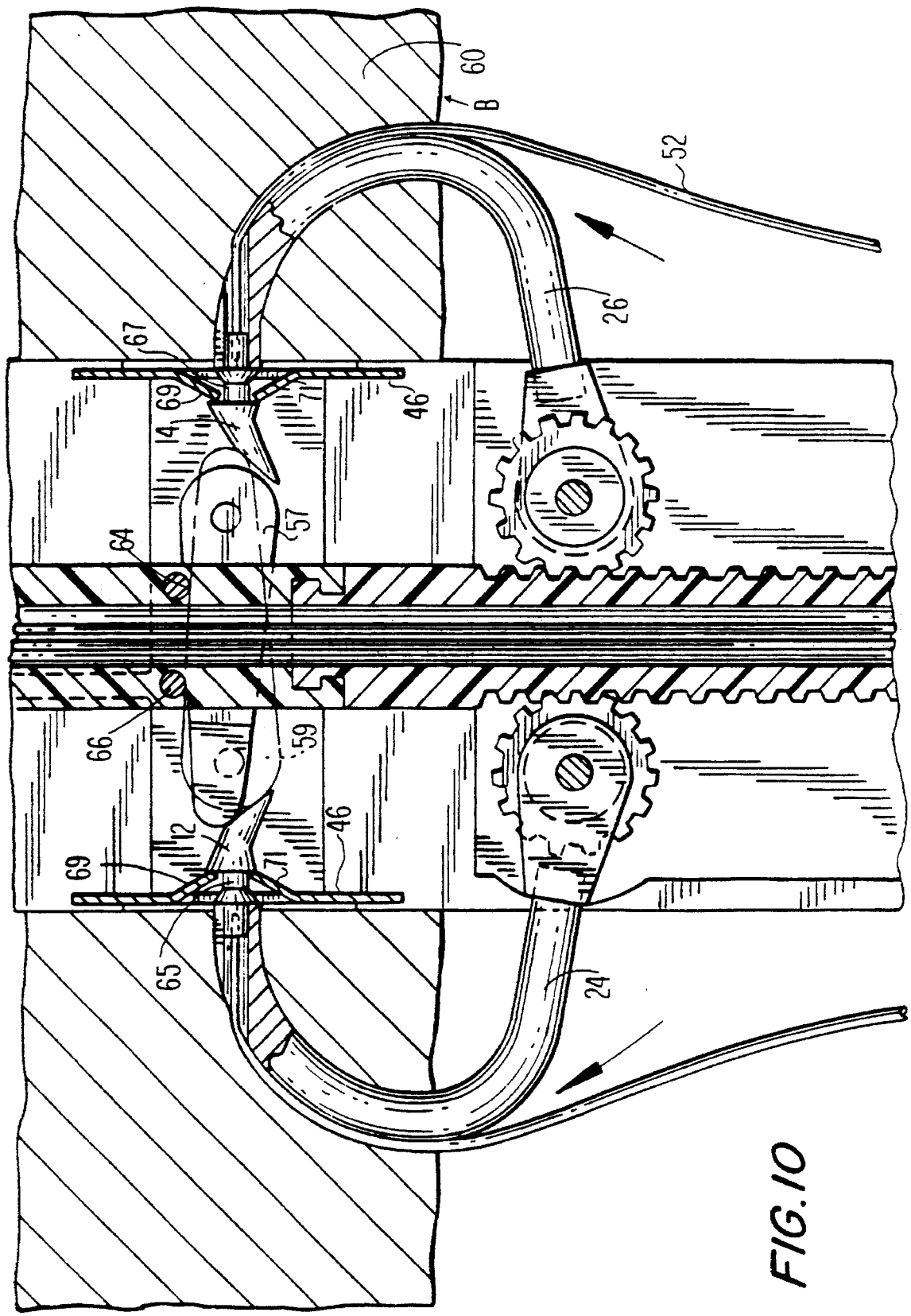
FIG. 10 is an enlarged view of the needle deployment mechanism showing the needle carriers in the fully deployed position.

Upon complete depression of actuator button 18, needles 12 and 14 become latched in latch members 46. One way of achieving the latching is shown as the pointed end passes through the gap between flap portions 65 and 67 and cam flap portions open until they seat in annular groove portions 65 and 67 of needles 12 and 14, as best shown in FIG. 10. To insure that needles 12 and 14 are retained in latch members 46, a needle kinking mechanism is preferably incorporated in the instrument and constructed to automatically strike the pointed ends of the needles as soon as they are completely within latch members 46. When actuator button 18 is completely depressed, camming pins 66 and 64, which are mounted on elongated rod 36, contact pivot arms 57 and 59 causing them to pivot distally and thus strike the pointed ends of needles 12 and 14, thereby deforming them, as shown in FIG. 10.

Figure 14:
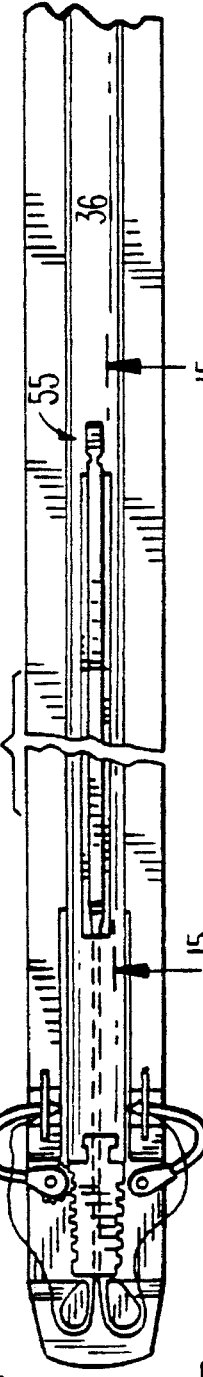
FIG. 14 is a view similar to FIG. 12, which shows the suture tensioning system after the deployment of the needles.
Figure 15:
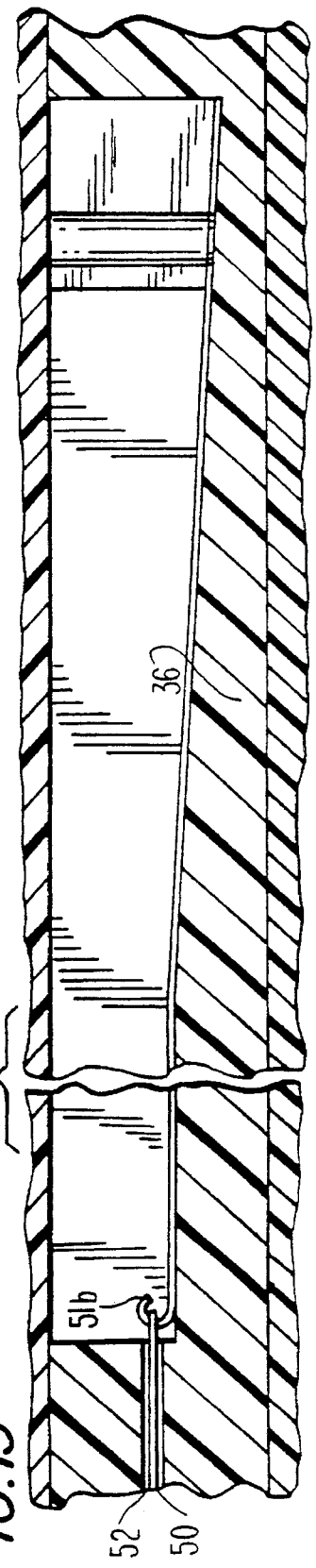
FIG. 15 is a cross-sectional view taken along section line 15—15 of FIG. 14.

The complete depression of actuator button 18 and the corresponding distal movement of elongated rod 36 and fully deployed position of needle carrier arms 24 and 26 causes suture material 52 to pull rolled spring element 51 (FIGS. 14 and 15) to completely unravel and release suture material 52 therefrom. In FIG. 15 rolled spring element is shown an instant before needle carrier arms reach their fully deployed position. At true full deployment of needle carrier arms 24 and 26, end 51b of rolled spring element releases suture material 52 so that it may be passed through the path created in fascia 60 by needles 12 and 14.

Figure 11:
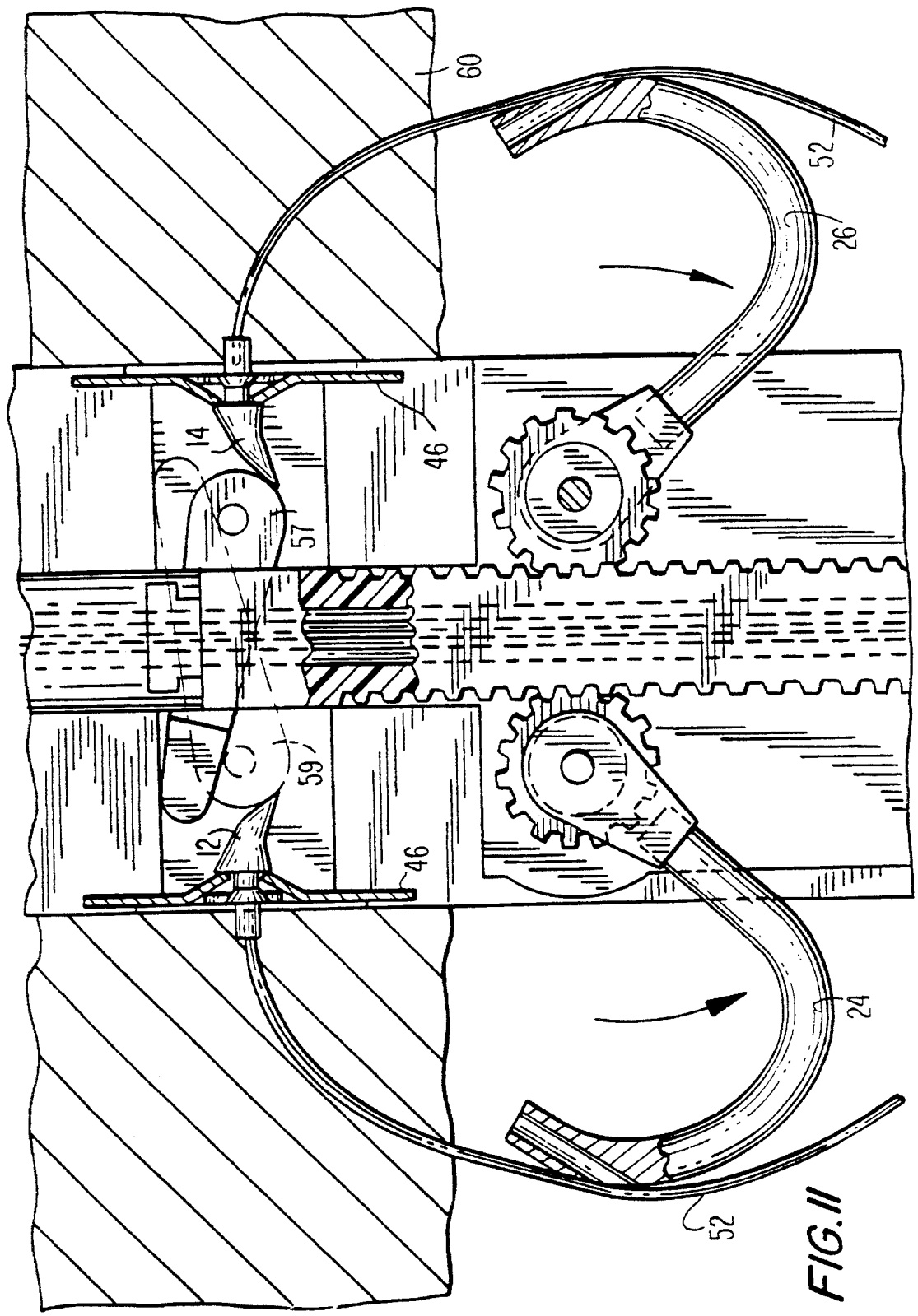
FIG. 11 is an enlarged view similar to FIG. 10, which shows the needle carriers retracting after the needles have become embedded in the needle retaining members.

Actuator button 18 is released allowing elongated rod 36 to return to its proximal or initial position and needle carrier arms 24 and 26 to return to their retracted positions within elongated housing portion 16 leaving needles 12 and 14 attached to latch members 46, as shown in FIG. 11. Suturing instrument 10 is pulled out of the trocar incision causing suture 52 (still attached to needles 12 and 14 which are latched onto suturing instrument 10) to be pulled through fascia 60 following the path taken by needles 12 and 14 and up through the remainder of the trocar incision until exiting the opening at the surface of the skin. Suture 52 is grasped and preferably cut away from needles 12 and 14 and thereafter tied off in the appropriate surgeon's knot.

Figure 17:
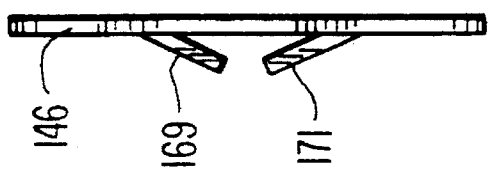
FIGS. 16–19 illustrate two alternative needle retaining members for use with the instrument of the present invention.
Figure 19:
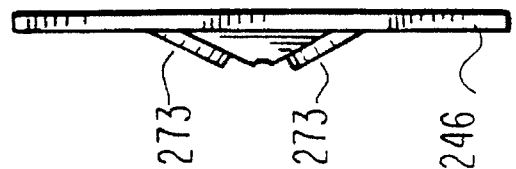
Figure 16:
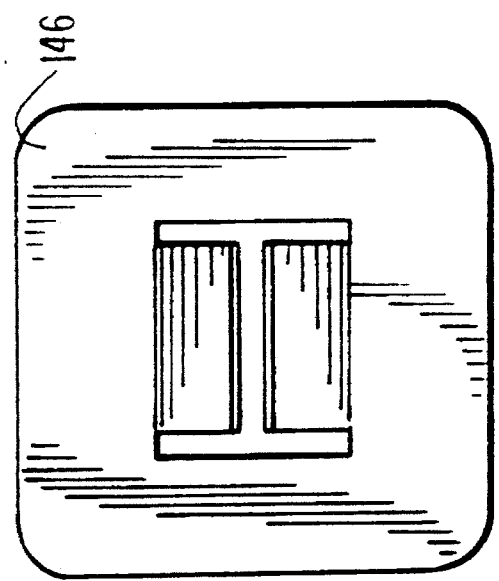
Figure 18:
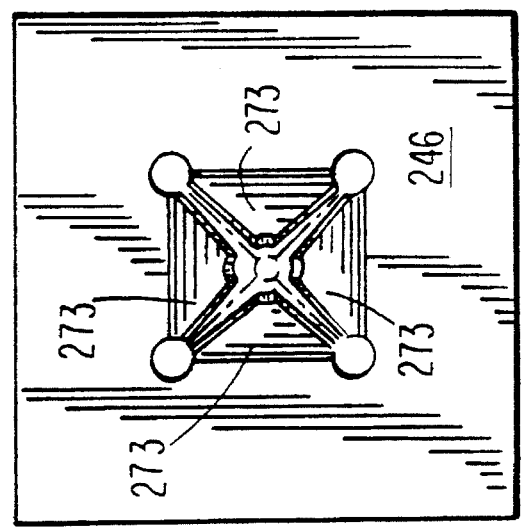

FIGS. 16–19 illustrate alternative embodiments of the needle latch member of the present invention. In FIGS. 16 and 17 latch member 146 is shown having flap portions 169 and 171 which are oriented at 90 degrees relative to flap members 69 and 71 of latch member 46. FIGS. 18 and 19 illustrate latch member 246 having four flap portions 273 orthogonally situated so as to receive the pointed end of needles 12 and 14 through the central region thereof.

Figure 20:
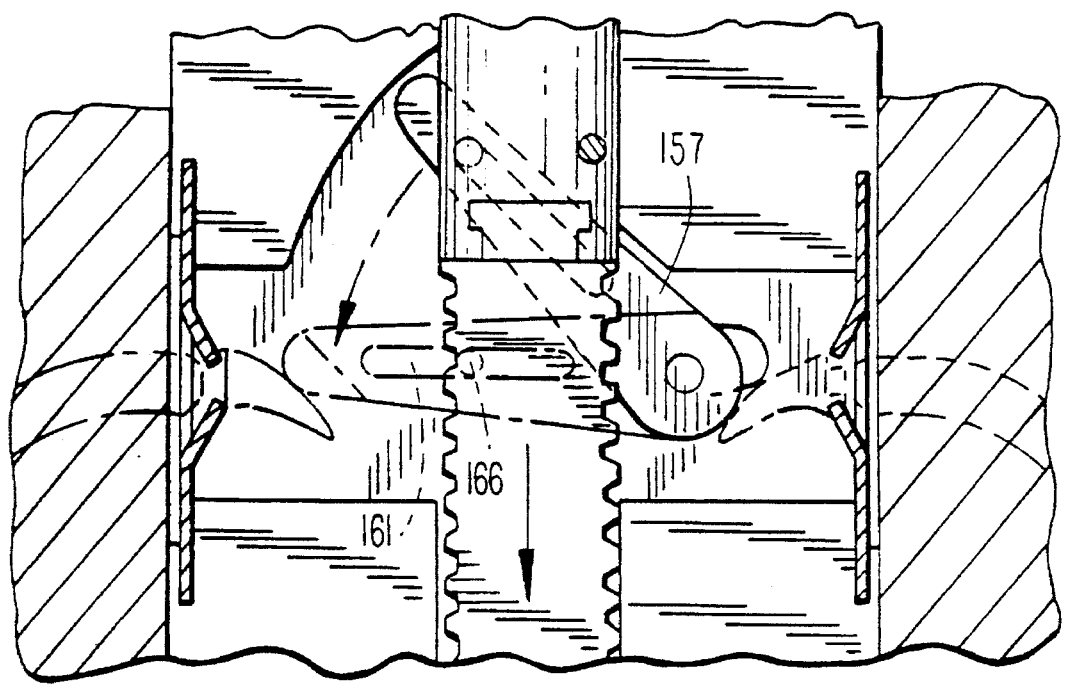
FIG. 20 is another embodiment of the needle skewing mechanism for use with the instrument of the present invention.

FIG. 20 illustrates an alternative embodiment of the arm component of the needle skewing mechanism of the present invention. Arm 157 is shown having camming slot 161 formed thereon so that camming pin 166 is in constant sliding contact with arm 157 as compared with the momentary sliding contact camming pins 64 and 66 have with arms 57 and 59.

Figure 21:
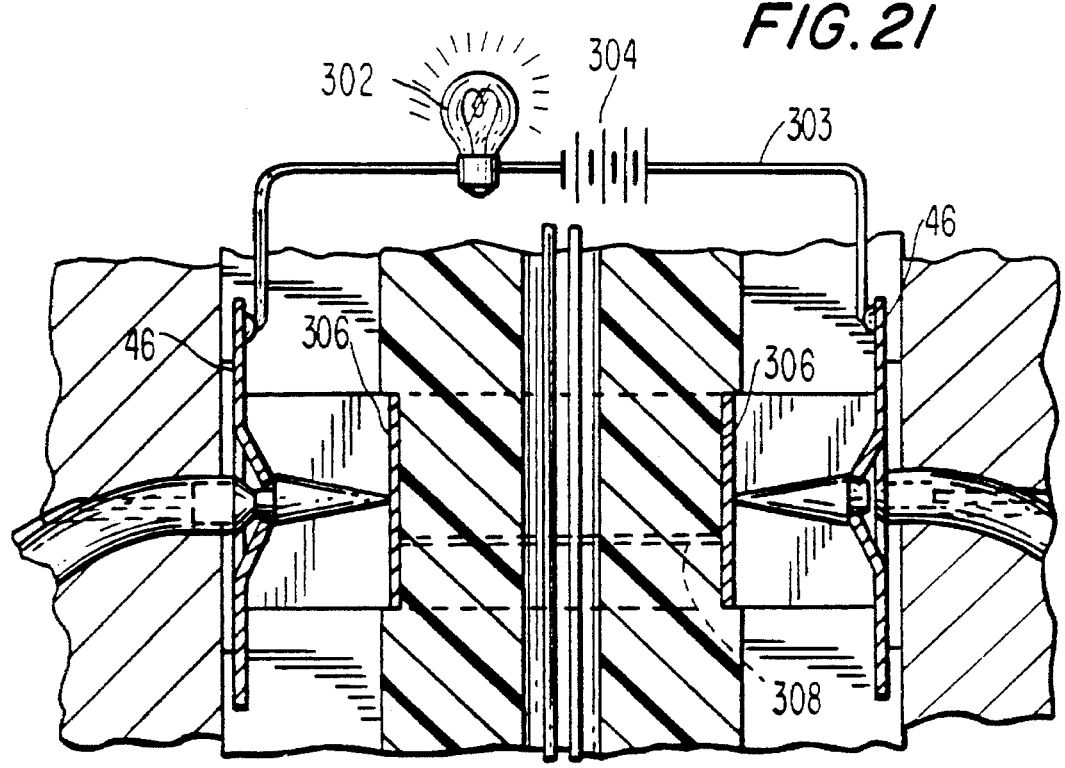
FIG. 21 illustrates the deployment indicator for the instrument of the present invention.

In FIG. 21 a needle deployment indicator is illustrated schematically with indicator light 302 being connected in a simple series circuit by wire 303 with a power source, such as battery 304 and latch members 46. The circuit is complete when the pointed ends of needles 12 and 14, which are electrically conductive, contact the electrically conductive plates 306 which are in turn connected by bridge wire 308.

The indicator light 302 is preferably positioned adjacent a proximal portion of the instrument to visually indicate to the user that the needles are securely embedded in latch members 46. Thus the connecting wires 303 would extend the length of the elongated body 16. Alternately, the indicator can be positioned adjacent a distal end of the elongated body 16, and if a visual indicator is provided, it can be viewed on the TV monitor used in the laparoscopic procedure.

The indicator is preferably an LED, however other devices which emit a detectable response to an electrical current can also be utilized, such as incandescent lamps, liquid crystal displays (LCD's), audible indicators, tactile indicators and light/temperature responsive materials.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed is:

1. A surgical instrument for applying sutures through body tissue, which comprises:

(a) an elongated body having a proximal end portion and a distal end portion;

(b) at least one needle carrier member operatively mounted in said distal end portion and movable between at least a retracted position and a deployed position;

(c) a needle having a tapered end and being releasably retained in said at least one needle carrier member such that when said at least one needle carrier member is in said retracted position said tapered end is prevented from contacting tissue;

(d) a predetermined length of suture material having one end affixed to said needle; and (e) a suture material tensioning member movably disposed within said elongated body for maintaining said suture material in tension during movement of said at least one needle carrier member from said retracted position to said deployed position.

2. A surgical instrument recited in claim 1, wherein said suture material tensioning member is a spring.

3. A surgical instrument recited in claim 1, wherein said suture material tensioning member is a constant force spring such that upon deployment of said suture material the amount of force necessary to move said spring remains uniform.

4. A surgical instrument recited in claim 1, further comprising a retaining mechanism operatively associated with said at least one needle carrier member and configured and dimensioned to retain said at least one needle carrier member in a partially deployed position located between said retracted position and said deployed position.

5. A surgical instrument recited in claim 1, further comprising a needle retaining mechanism disposed in said elongated body and configured and dimensioned to retain said needle therein when said at least one needle carrier mechanism is moved to said deployed position.

6. A surgical instrument according to claim 1, further comprising a deployment indicator configured and dimensioned to provide an indication to an operator of said instrument when said at least one needle carrier member is in said deployed position.

7. A surgical instrument for applying sutures through body tissue, which comprises:

(a) an elongated body having a proximal end portion and a distal end portion;

(b) at least one needle carrier member operatively mounted in said distal end portion and movable between at least a retracted position and a deployed position;

(c) a needle releasably retained in said at least one needle carrier;

(d) a predetermined length of suture material having one end affixed to said needle;

(e) a suture material tensioning member disposed within said elongated body for maintaining said suture material in tension during movement of said at least one needle carrier member from said retracted position to said deployed position; and (f) an actuator member operatively associated with said at least one needle carrier member, said actuator member being movable between at least a first position and a second position to move said at least one needle carrier from said retracted position to said deployed position and a needle skewing mechanism operatively associated with said actuator member such that upon movement of said actuator member from said first position to said second position said needle skewing mechanism contacts a tapered portion of said needle to change the alignment thereof relative to said retaining member.

8. A surgical instrument for applying sutures through body tissue, which comprises:

(a) an elongated body having a proximal portion and a distal portion, (b) at least one needle carrier member operatively mounted in said distal end portion and movable between at least an initial position, a partially deployed position and a fully deployed position;

(c) a needle releasably retained at a predetermined position with respect to said at least one needle carrier as said needle carrier moves from the initial position to the fully deployed position;

(d) an actuator member engaging said at least one needle carrier member, said actuator member being movable between at least a first position and a second position to move said at least one needle carrier from said initial position to said fully deployed position;

(e) a predetermined length of suture material having one end thereof affixed to said needle; and (f) a needle carrier retaining mechanism operatively associated with said at least one needle carrier member, said needle carrier retaining mechanism being configured and dimensioned to retain said at least one needle carrier in said partially deployed position.

9. A surgical instrument as recited in claim 8, wherein said needle carrier retaining mechanism includes a latch member mounted on said elongated body and a post member operatively associated with said at least one needle carrier member and movable in relation to said latch member, whereby upon movement of said at least one needle carrier member to said partially deployed position said post member engages said latch member and is releasably retained therein such that said at least one needle carrier member is releasably retained in said partially deployed position.

10. A surgical instrument as recited in claim 8, further comprising an actuator member operatively associated with said at least one needle carrier member and said needle carrier retaining mechanism, said actuator member being movable between at least a first position and a second position to move said at least one needle carrier member into said initial position, said partially deployed position and said fully deployed position.

11. A surgical instrument as recited in claim 10, wherein said actuator member is biased toward said first position.

12. A surgical instrument as recited in claim 10, wherein said needle carrier retaining mechanism includes a latch member operatively associated with said elongated body and a post member mounted on said actuator member and operatively associated with said latch member.

13. A surgical instrument as recited in claim 12, wherein said latch member is mounted on a pivot arm.

14. A surgical instrument as recited in claim 13, wherein said pivot arm is biased to maintain said latch member in a predetermined orientation.

15. A surgical instrument as recited in claim 14, wherein said latch member is configured and dimensioned such that upon movement of said actuator member from said first position toward said second position, said post member releasably engages said latch member whereby said actuator member is releasably held at a predetermined distance between said first and second positions.

16. A surgical instrument as recited in claim 15, wherein upon further movement of said actuator member toward said second position said post member disengages said latch member.

17. A surgical instrument as recited in claim 16, wherein said actuator member is biased toward said first position, whereby upon release of said actuator member when said actuator member is in said second position, said at least one need carrier member returns to said initial position.

18. A surgical instrument as recited in claim 8, further comprising a needle retaining mechanism disposed in said elongated body and configured and dimensioned to retain said needle therein when said at least one needle carrier member is in said deployed position.

19. A surgical instrument as recited in claim 18, further comprising a needle skewing mechanism disposed adjacent said needle retaining mechanism movable from a first position to a second position to change the alignment of said needle relative to said retaining member.

20. A surgical instrument for applying sutures through body tissue, which comprises:
   (a) an elongated body having a proximal portion and a distal portion;
   (b) at least one needle carrier member operatively associated with said distal portion and movable between at least an initial position and a deployed position;
   (c) an actuator member operatively associated with said at least one needle carrier member, said actuator member being movable between at least a first position and a second position to move said at least one needle carrier from said initial position to said deployed position;
   (d) a needle releasably retained in said at least one needle carrier member;
   (e) a needle retaining member disposed in said elongated body and adapted to retain said needle therein when said at least one needle carrier member is in said deployed position; and
   (f) a needle skewing mechanism operatively associated with said actuator member for changing the alignment of the needle relative to said retaining member.

21. A surgical instrument as recited in claim 20, wherein upon movement of said actuator member from said first position to said second positions said needle skewing mechanism contacts a tapered portion of said needle.

22. A surgical instrument as recited in claim 21, wherein said needle skewing mechanism includes at least one arm member moveable between at least an initial position and a final position, said arm member being operatively associated with said actuator member, whereby upon movement of said actuator member from said first position to said second position said arm member is moved from said initial position to said final position.

23. A surgical instrument as recited in claim 22, wherein said needle skewing mechanism further includes a camming pin which is mounted on said actuator member such that said camming pin contacts Said arm member when said actuator member is moved from said first position to said second position.

24. A surgical instrument as recited in claim 22, wherein said needle skewing mechanism further includes a camming pin mounted on said actuator member and a slot formed in said arm member such that said camming pin travels in said slot when said actuator member is moved from said first position to said second position.

25. A surgical instrument as recited in claim 20, further comprising a deployment indicator operatively associated with said distal elongated body distal portion and configured and dimensioned to provide an indication to an operator of said instrument when said at least one needle carrier member is in said second position.

26. A surgical instrument for applying sutures through body tissue, which comprises:
   (a) an elongated body having a proximal portion and a distal portion;
   (b) at least one needle carrier member operatively associated with said distal portion of said body portion, said at least one needle carrier member movable between at least a first position and a second position;
   (c) a needle member having a tapered end and being releasably retained in said at least one needle carrier member such that when said at least one needle carrier member is in said first position said tapered end is prevented from contacting tissue; and
   (d) an illuminating indicator configured and dimensioned to provide an indication to an operator of said instrument when said at least one needle carrier member is in said second position.

27. A surgical instrument as recited in claim 26, wherein said indicator is a deployment indicator and includes an illuminating member which illuminates when said at least one needle carrier member is moved to said second position.

28. A surgical instrument as recited in claim 27, wherein said illuminating member is a light bulb connected in a series circuit with a power source, said circuit being closed when said at least one needle carrier member is in said second position.

* * * * *